US008542363B2

(12) United States Patent
Wynn et al.

(10) Patent No.: US 8,542,363 B2
(45) Date of Patent: Sep. 24, 2013

(54) SELF-ALIGNING LIGHT SOURCE AND DETECTOR ASSEMBLY FOR ABSORBANCE MEASUREMENT

(75) Inventors: William H. Wynn, San Carlos, CA (US); Michael Weiss, Gerlingen (DE); Guido Mertens, Blomberg (DE)

(73) Assignee: Endress + Hauser Conducta Inc., Greenwood, IN (US)

( * ) Notice: Subject to any disclaimer, the term of this patent is extended or adjusted under 35 U.S.C. 154(b) by 280 days.

(21) Appl. No.: 12/975,597

(22) Filed: Dec. 22, 2010

(65) Prior Publication Data

US 2012/0162650 A1  Jun. 28, 2012

(51) Int. Cl.
*G01N 21/00* (2006.01)
(52) U.S. Cl.
USPC .......................................... 356/440; 356/246
(58) Field of Classification Search
USPC ................. 356/432, 440, 246, 244
See application file for complete search history.

(56) References Cited

U.S. PATENT DOCUMENTS

| 3,847,482 | A | * | 11/1974 | Sokol et al. ..................... 356/40 |
| 3,881,827 | A | * | 5/1975 | Gilford et al. ................ 356/246 |
| 4,501,491 | A | * | 2/1985 | Breda et al. .................... 356/39 |
| 4,890,920 | A | * | 1/1990 | Niziolek et al. .............. 356/336 |
| 5,206,711 | A | * | 4/1993 | Berthold et al. ............. 356/436 |
| 5,320,808 | A | * | 6/1994 | Holen et al. ................... 422/64 |
| 2006/0290944 | A1 | * | 12/2006 | Arnott et al. ................. 356/519 |
| 2007/0024847 | A1 | * | 2/2007 | Zambuto et al. ............. 356/300 |
| 2010/0078581 | A1 | * | 4/2010 | Trottier ......................... 250/577 |
| 2012/0061579 | A1 | * | 3/2012 | Wynn ............................ 250/372 |

* cited by examiner

*Primary Examiner* — Tarifur Chowdhury
*Assistant Examiner* — Michael P Lapage
(74) *Attorney, Agent, or Firm* — Bacon & Thomas, PLLC

(57) ABSTRACT

Self-aligning light source and detector assembly having a sensor support mounted in a predetermined, fixed position, a light source holder mounted in a predetermined, fixed position relative to the sensor support, a sensor mounted in a fixed position on the sensor support, and a lamp assembly removably mounted to the light source holder in a predetermined position defined by mating surfaces which engage each other and seat the lamp assembly in the predetermined position whenever the lamp assembly is installed in the holder.

3 Claims, 3 Drawing Sheets

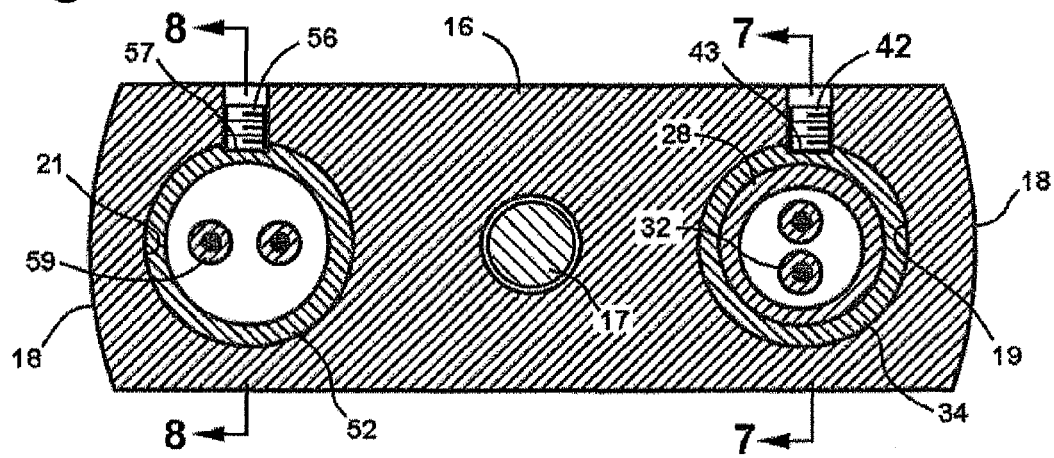
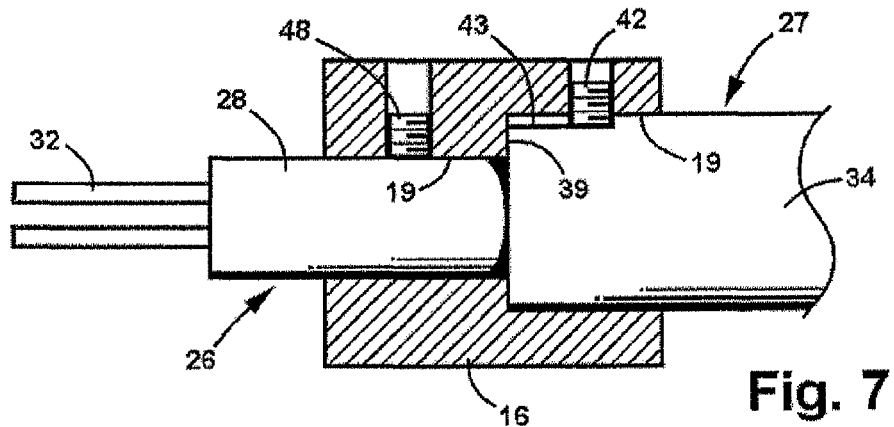
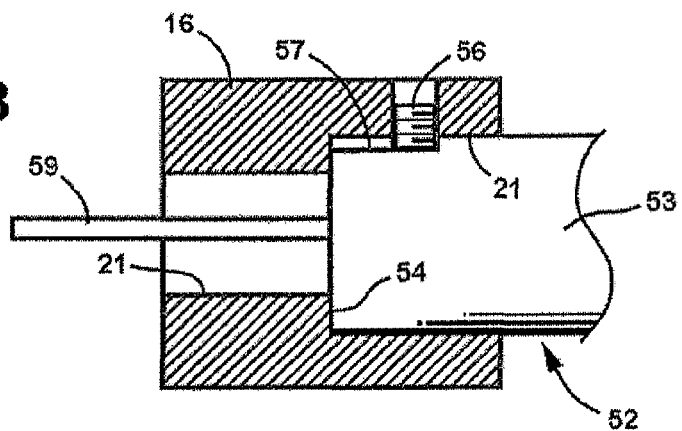

SELF-ALIGNING LIGHT SOURCE AND DETECTOR ASSEMBLY FOR ABSORBANCE MEASUREMENT

BACKGROUND OF THE INVENTION

1. Field of Invention

This invention pertains generally to the measurement of optical absorbance and, more particularly, to a self-aligning light source and detector assembly for use in measuring optical absorbance.

2. Related Art

Instruments for measuring optical absorbance are widely used in fields such as industrial, medical, and food applications. Such instruments generally include a light source and a detector, and for consistent, reliable readings, it is important that the light source and detector remain in proper alignment, particularly when the instruments are used in critical applications.

Light sources such as incandescent lamps tend to burn out and require periodic replacement, which can easily result in improper alignment between light source and detector, particularly in smaller, more compact instruments. If the light source cannot be replaced in the field, then the instrument either has to be replaced or removed from service and sent away for repair, both of which can be expensive and disruptive.

OBJECTS AND SUMMARY OF THE INVENTION

It is, in general, an object of the invention to provide a new and improved light source and detector assembly for use in measuring optical absorbance.

Another object of the invention is to provide a light source and detector assembly of the above character, in which the light source and detector are self-aligning.

These and other objects are achieved in accordance with the invention by providing a self-aligning light source and detector assembly having a sensor support mounted in a predetermined, fixed position, a light source holder mounted in a predetermined, fixed position relative to the sensor support, a sensor mounted in a fixed position on the sensor support, and a lamp assembly removably mounted to the light source holder in a predetermined position defined by mating surfaces which engage each other and seat the lamp assembly in the predetermined position whenever the lamp assembly is installed in the holder.

BRIEF DESCRIPTION OF THE DRAWINGS

FIG. 6 is a vertical sectional view of the mounting block and associated components in the embodiment of FIG. 1.

FIG. 7 is a cross-sectional view taken along line 7-7 in FIG. 6.

FIG. 8 is a cross-sectional view taken along line 8-8 in FIG. 6.

DETAILED DESCRIPTION

Figure 1:
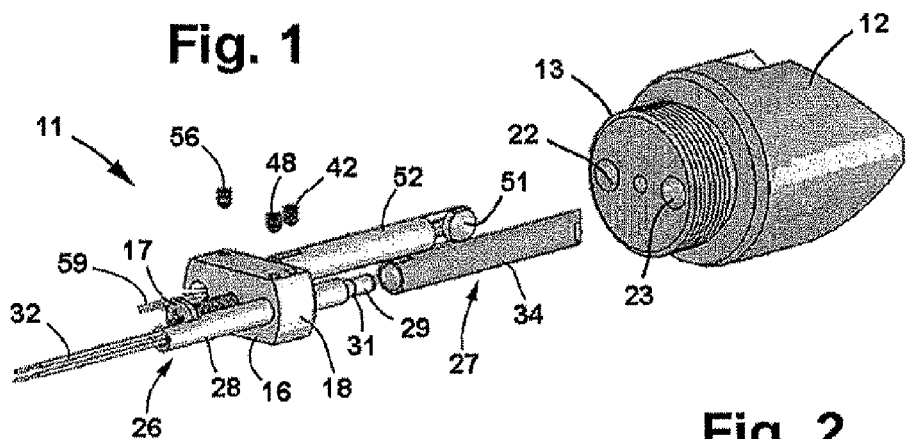
FIG. 1 is an exploded isometric view of one embodiment of a self-aligning light source and detector assembly according to the invention.
Figure 2:
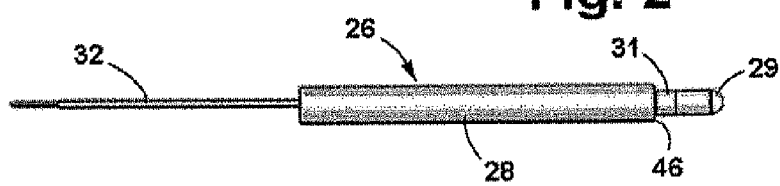
FIG. 2 is a top plan view of the lamp assembly in the embodiment of FIG. 1.
Figure 3:
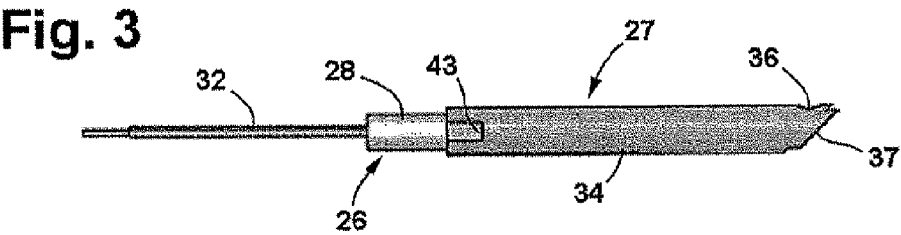
FIG. 3 is a top plan view of the assembled light source in the embodiment of FIG. 1.
Figure 4:
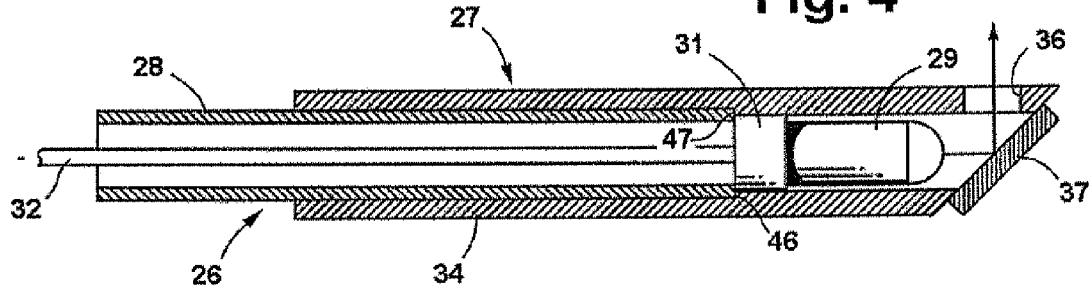
FIG. 4 is an enlarged, fragmentary sectional view of the assembled light source.

In FIG. 1, the light source and detector assembly 11 is illustrated in connection with a probe head 12 having an externally threaded base 13 that attaches to a generally cylindrical housing (not shown). A mounting block 16 is attached to the inner face of the base 13 by a mounting screw 17. The block is generally rectangular, with arcuately curved end surfaces 18 of slightly smaller diameter than the inner wall of the housing. Axially extending parallel bores 19, 21 extend through the mounting block on opposite sides of the mounting screw in alignment with corresponding bores 22, 23 in the base.

The probe head 12 can as well be designed to attach to a disposable container, such as for example a disposable fermentation bag having flexible walls for single-use in a biotechnological process. In this case the threaded base 13 can be attached to a fixture in the disposable container wall or the base 13 can be designed to be welded to the wall of the disposable container.

The light source consists of a lamp assembly 26 which is removably mounted in a tubular holder 27. The tube holder is mounted in bore 19, passes through bore 22, and extends from the outer end of the probe head 12. The lamp assembly includes an elongated tubular body 28, with a lamp 29 mounted in a socket 31 at one end thereof and leads 32 extending from the socket, through the tubular body for connection to a power source in the probe housing.

The lamp holder has a tubular body 34 with an aperture 36 in the side wall thereof toward the distal or outer end of the tube and a mirror 37 mounted in the distal end portion of the tube for directing light from the lamp through the aperture toward the sensor. In the embodiment illustrated, the mirror is inclined at an angle of 45 degrees to the axis of the lamp holder, and the light from the lamp is reflected in a direction perpendicular to that axis. The aperture 36 can be tightly covered by a transparent window, e.g. made of quartz, sapphire or a transparent plastic depending on the wavelength used for measurement.

The inner end of the lamp holder abuts against a radial shoulder 39 in bore 19 and is secured in place by a set screw 42 in the mounting block which is received in a key way or notch 43 in the outer wall of the lamp holder tube. Thus, when the inner end portion of the tube is inserted in the bore in abutting engagement with the shoulder and the set screw is tightened in the key way, the lamp holder is locked in a predetermined, fixed position both axially and rotatively relative to the mounting block and the probe head.

The lamp assembly is inserted coaxially into the lamp holder through the inner end of the lamp holder tube and has a radial shoulder 46 which abuts against a corresponding shoulder 47 in the tube. The lamp assembly is locked in position in the lamp holder by a set screw 48 in the mounting block which is tightened against the outer wall of the tube. Thus, the lamp assembly can be removed from the holder and then reinserted and locked in a predetermined axial position. The inner end portion of the lamp assembly projects from the inner end of the holder and can be used for rotating the lamp assembly within the holder and mount for maximum optical signal before seating the set screw.

The detector assembly includes a light detector or sensing element 51 and a sensor support 52. The sensor support has an elongated tubular body 53 which is mounted in bore 21, passes through bore 23, and extends from the outer end of the probe head. The inner end of the support tube abuts against a radial shoulder 54 in bore 21 and is secured in place by a set screw 56 in the mounting block. This set screw is received in a key way or notch 57 in the outer wall of the support tube. Thus, when the inner end portion of the tube is inserted in the bore in abutting engagement with the shoulder and the set screw is tightened in the key way, the sensor support is locked in a predetermined, fixed position both axially and rotatively relative to the mounting block, the probe head, and the light source.

Light detector or sensing element 51 is mounted on the side wall of the support tube near the distal end of the tube directly opposite and facing the aperture and mirror in the lamp holder, with leads 59 from the sensing element extending through the tube for connection to circuitry in the probe housing.

Figure 5:
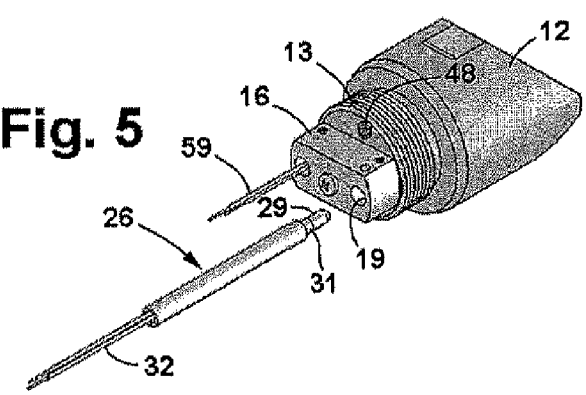
FIG. 5 is an isometric view of the embodiment of FIG. 1 with the lamp assembly removed for replacement of the lamp

To replace the lamp, the probe head is separated from the housing, the set screw 48 is removed, and the lamp assembly is withdrawn from the inner end of the lamp holder, as illustrated in FIG. 5. The old lamp is removed from the socket, and a new lamp is installed in its place. The lamp assembly is then reinserted into the holder until shoulder 46 abuts against shoulder 47 and turned to maximize the signal from the detector. With the lamp assembly thus seated in its predetermined position and oriented for best signal, set screw 48 is tightened against the lamp assembly to lock it in place.

The lengths of the lamp holder and the detector assembly are such that when the inner ends of the lamp holder and sensor support tubes are seated against the shoulders in the mounting block bores and the set screws are tightened in the key ways, the sensing element is directly opposite the aperture in the lamp holder, and light reflected from the lamp by the mirror is focused on the sensing element. The alignment is self-guided and will always be the same whether the device is assembled in the factory or serviced in the field.

The alignment of the light source and sensor is not disturbed by replacement of the lamp, since neither the lamp holder nor the detector assembly is moved during the process. Even if one of them did happen to move, it is easily returned its self-aligning position.

The invention has a number of important features and advantages. The light source and detector are self-aligning, and the light source lamp can be replaced in the field without disturbing that alignment.

The lamp assembly is independent of the lamp holder and projection mirror. The lamp assembly can easily be removed for lamp replacement without removal of the lamp holder and mirror which are affixed to the mounting block and probe head. The lengths of the lamp holder and the detector assembly are fixed so that when each assembly is inserted into the mounting block, its position is controlled and the two assemblies are automatically aligned to each other.

Figure 9:
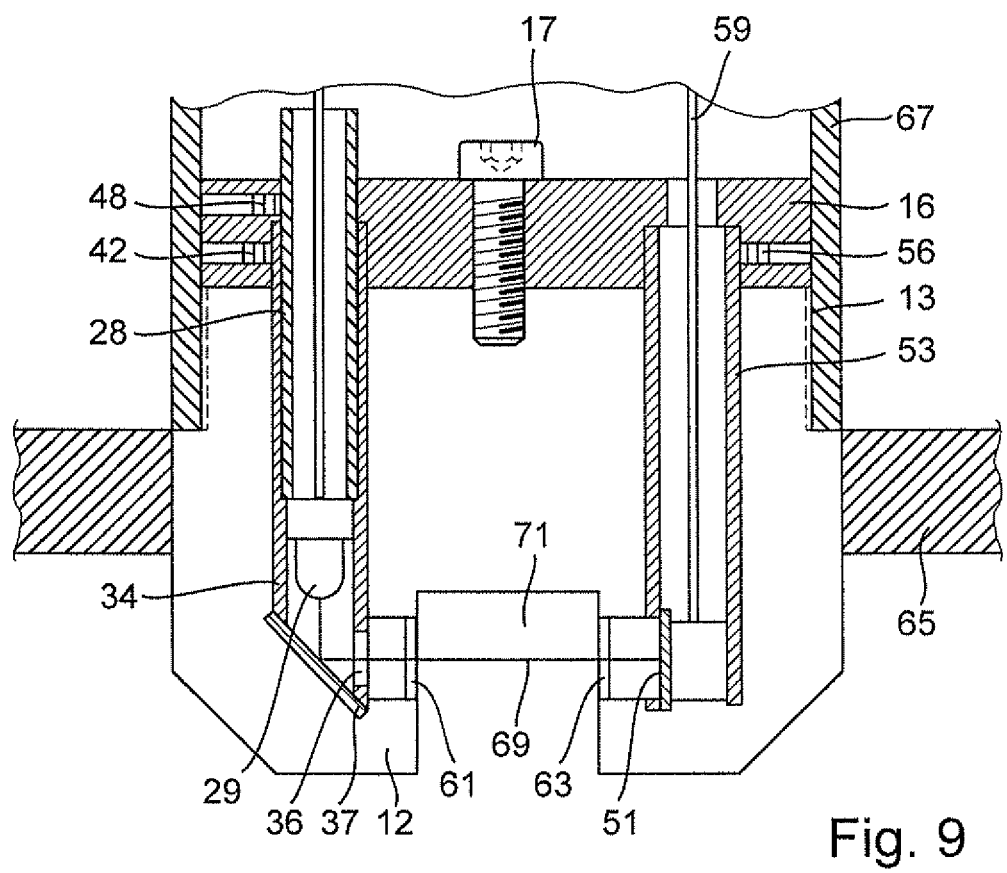
FIG. 9 shows the complete probe assembly including the lamp holder and the detector holder mounted in the mounting block.

The mounting block 16 with the lamp assembly fixed in bore 19 and the detector assembly fixed in bore 21 forms a readily aligned optical assembly. This assembly can be connected to various different kinds of probe heads as long as they provide an appropriate base with bores corresponding to both the tubular holder 27 of the lamp assembly and the tubular holder 53 of the detector assembly. FIG. 9 shows the complete probe assembly with the lamp holder and the detector holder mounted in the mounting block 16, which is fixed to the probe head 12. The threaded base 13 of the probe head 12 is screwed to a cylindrical probe housing 67.

In this example, the sensor assembly and the detector assembly do not protrude from the probe head 12. Instead, the probe head 12 comprises two facing apertures which provide a passage for a light beam 69 reflected from mirror 37. In order to protect the lamp 29 and the sensing element 51 from medium comprised in the gap 71 through which light beam 69 travels, the apertures are sealingly closed by windows 61 and 63. Windows 61 and 63 can be made of any material_transparent for the light emitted by the lamp 29. For example, they can be made of quartz, quartz glass, sapphire or transparent plastics.

The probe head 12 is connected to a container wall 65 of a container comprising a medium, for example a liquid or a liquid mixture used in an industrial process. In pharmaceutical or biotechnological processes often single-use containers, so-called disposable containers, are used. These disposable containers are usually made of plastics that can be sterilized before starting the pharmaceutical or biotechnological process and that can be disposed of after the process has been completed. Disposable containers can be rigid or flexible tubes or flexible bags, for example disposable fermenters. The container wall 65 can be glued or welded to the probe head 12. It can also comprise a fixture comprising for example a bayonet fitting or an internal thread for receiving the probe head 12.

In this way, the readily aligned optical assembly comprising the mounting block 16 with the lamp assembly fixed in bore 19 and the detector assembly fixed in bore 21 can be used several times with different disposable containers having a corresponding probe head 12 fixed in or connected to a container wall 65. After use the probe heads can be disposed of together with the container. The expensive optical assembly, however, can be used again.

It is apparent from the foregoing that a new and improved self-aligning light source and detector assembly has been provided. While only certain presently preferred embodiments have been described in detail, as will be apparent to those familiar with the art, certain changes and modifications can be made without departing from the scope of the invention as defined by the following claims.

The invention claimed is:

1. A measuring system for absorbance measurements in a process medium, in particular in a pharmaceutical or biotechnological process, comprising:
   a disposable container in which the process medium is received, the container comprising a container wall, in which a probe head is accomodated, said probe head comprising a first bore for receiving a light source holder and a second bore for receiving a sensor support;
   a light source and detector assembly, comprising the light source holder and said sensor support mounted in a mounting block in a predetermined, fixed position relative to each other, a lamp assembly mounted to said light source holder in a predetermined position and a detector mounted in a fixed position on said sensor support, wherein:
   said light source holder and said sensor support are received in said first and second bore of said probe head respectively, and
       said probe head comprises apertures providing a light beam passageway between said lamp assembly and said detector.

2. The measuring system of claim 1, wherein:
   said light source and said detector assembly is removably attached to said probe head.

3. The measuring system of claim 1, wherein:
   said container comprises a flexible container wall.

* * * * *